(12) United States Patent  
Fabiano et al.

(10) Patent No.: US 8,277,839 B2
(45) Date of Patent: Oct. 2, 2012

(54) ORAL PHARMACEUTICAL COMPOSITION OF ANILINOPYRIMIDINE, PREPARATION AND USE THEREOF

(75) Inventors: Santa Fabiano, Casoria (IT); Mario Maio, Tivoli (IT)

(73) Assignee: Ares Trading S.A., Aubonne (CH)

( * ) Notice: Subject to any disclaimer, the term of this patent is extended or adjusted under 35 U.S.C. 154(b) by 594 days.

(21) Appl. No.: 12/307,605

(22) PCT Filed: Jul. 5, 2007

(86) PCT No.: PCT/EP2007/056859
§ 371 (c)(1),
(2), (4) Date: Jun. 18, 2009

(87) PCT Pub. No.: WO2008/003769
PCT Pub. Date: Jan. 10, 2008

(65) Prior Publication Data
US 2009/0324711 A1    Dec. 31, 2009

Related U.S. Application Data

(60) Provisional application No. 60/818,831, filed on Jul. 6, 2006.

(30) Foreign Application Priority Data

Jul. 10, 2006   (EP) ..................... 06116903

(51) Int. Cl.
*A61K 9/66* (2006.01)
*A61K 31/497* (2006.01)
*A61P 35/04* (2006.01)

(52) U.S. Cl. ................... 424/455; 514/252.14
(58) Field of Classification Search ........................ None
See application file for complete search history.

(56) References Cited

U.S. PATENT DOCUMENTS

| 4,910,021 | A | * | 3/1990 | Davis et al. | 424/456 |
| 5,554,384 | A | * | 9/1996 | Samuels et al. | 424/451 |
| 2002/0115690 | A1 | * | 8/2002 | Chen et al. | 514/336 |
| 2003/0203926 | A1 | * | 10/2003 | Kois et al. | 514/275 |
| 2005/0008697 | A1 | * | 1/2005 | Gorissen | 424/464 |
| 2006/0223743 | A1 | * | 10/2006 | Abel et al. | 514/7 |

FOREIGN PATENT DOCUMENTS

| WO | WO-02/46171 | 6/2002 |
| WO | WO 0246171 A2 * | 6/2002 |
| WO | WO 2006102157 A1 * | 9/2006 |

OTHER PUBLICATIONS

Frelin, Blood, 105, 2005.*
Zips, New Anticancer Agents, in vivo, 19, 2005.*
Frelin et al., Blood, 105(2):804-811 (2005).
International Search Report in PCT/EP2007/056859 dated Apr. 25, 2008.
Nangle et al. J. Urology, 68(1):214-218 (2006).
Oliver et al., Biochem. Pharmacol., 72, 1054-1068 (2006).

* cited by examiner

*Primary Examiner* — Robert A Wax
*Assistant Examiner* — William Craigo
(74) *Attorney, Agent, or Firm* — Marshall, Gerstein & Borun LLP

(57) ABSTRACT

An oral pharmaceutical composition comprising a capsule dosage form containing a liquid fill composition including an anilinopyrimidine derivative of Formula (I) and a pharmaceutically acceptable excipient selected from the group consisting of polyethylene glycol, a glyceryl ester of capric acid or a mixture thereof. The liquid fill composition is formulated in a hard gelatin capsules and can be used for the preparation of a medicament for the treatment of cancer in particular AML.

(I)

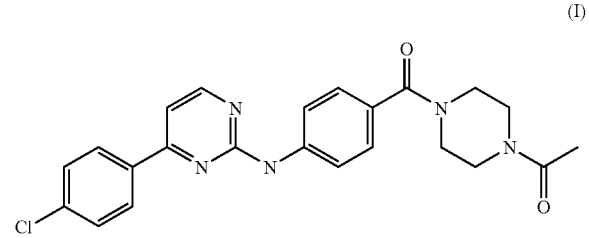

13 Claims, No Drawings

ORAL PHARMACEUTICAL COMPOSITION OF ANILINOPYRIMIDINE, PREPARATION AND USE THEREOF

CROSS-REFERENCE TO RELATED APPLICATIONS

This is the U.S. national phase application of International Application No. PCT/EP2007/056859, filed Jul. 5, 2007, which claims the benefit of U.S. provisional patent application No. 60/818,831, filed Jul. 6, 2006 and European patent application No. 06116903.3, filed Jul. 10, 2006.

TECHNICAL FIELD

The present invention relates to an oral pharmaceutical composition of the anilinopyrimidine derivative of Formula (I)

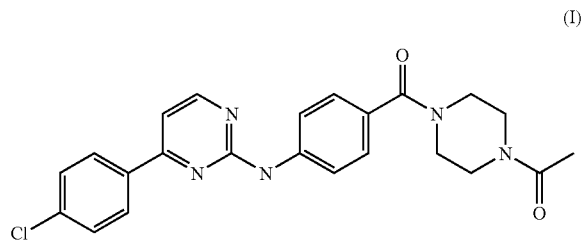

and the use of said oral pharmaceutical composition to treat cancer and in particular Acute Myeloid Leukemia (AML).

BACKGROUND ART

PCT WO/02/46171 describes a series of anilinopyrimidine derivatives and among them the anilinopyrimidine derivative having the formula: 1-(4{4-[4-(4-Chloro-phenyl)-pyrimidin-2-ylamino]-benzoyl}-piperazin-1-yl)-ethanone (see Formula (I) above).

Frelin and al. (Blood, 15 Jan. 2005 Volume 105, Number 2, pages 804-811) have show that AS602868, an anilinopyrimidine derivative corresponding to the compound of Formula I above and covered by the patent application No PCT WO/02/46171, induces cell death in most primary fresh cells from Acute Myeloid Leukemia (AML) patients. These results strongly suggest that pharmacologic inhibition of the NF-kB pathways could be an interesting adjuvant approach in future treatments for AML.

Acute Myeloid Leukemia (AML) is characterized by invasion of the bone marrow by leukemic myeloid blasts arrested at various maturation steps. Despite advances in diagnosis of the different subtypes of AML and progress in therapeutic approaches, current chemotherapies produce only initial remission. Relapse often occurs, and AML is finally fatal in more than 70% of cases. Dysregulation of malignant hematopoietic stem/progenitor cells (leukemic stem cells, LSCs) produces blast cells with differentiation defects. LSCs, which are quiescent or slowly cycling and therefore less sensitive to chemotherapy, are responsible for disease relapse and represent the target for future innovative therapies.

LSCs are both phenotypically and biologically similar to normal hematopoietic stem cells (HSCs), making discrimination and targeting difficult. One interesting difference is a constitutive activation of the nuclear factor-kB (NF-kB) transcription factor in LSC and AML blasts but not in HSCs. Such subnormal constitutive NF-kB activation has been detected in two other hematopoietic cancers, Hodgkin lymphoma and acute lymphoid leukemia, as well as in various solid tumors. Transcription factors of the NF-kB family are regulators of cell proliferation and survival and control expression of several genes relevant to the tumorigenic process.

For instance, NF-kB promotes cell survival through expression of gene coding for antiapoptotic proteins (cellular inhibitor of apoptosis protein-1, (c-IAP1), c-IAP2, bfl-1 and bcl-x1). NF-kB is also known to stimulate cell proliferation via induction of growth factors (interleukin-2 (IL-2), granulocyte-macrophage colony stimulating factor (GM-CSF)) or cell cycle regulators (cyclin D1 and c-myc). NF-kB could participate in the resistance of tumor cells to treatments after expression of the multidrug resistance (MDR) protein. NF-kB could promote metastasis through induction of the extracellular matrix-degrading enzymes matrix metalloproteinase 9 (MMP9) and urokinase-type plasminogen activator (uPA). In addition, most actual antineoplastic drugs also activate NF-kB, an event that interferes with the treatments.

It has therefore been proposed that inhibition of NF-kB could be an adjuvant therapy for cancer. NF-kB dimers are maintained inactive in the cytosol by inhibitory subunits of the IkB family. Upon cell triggering by a wide spectrum of stimuli, IkB molecules are phosphorilated on 2 critical serine residues by 2 highly related specific kinases, IKK1, or α, and IKK2, or β, which together with the scaffold protein IKKγ/NF-kB essential modulator (NEMO) form the IKK complex that integrates signals for NF-kB activation. Serine phosphorylation results in polyubiquitination of IkB and its subsequent degradation by proteasome. If transfection of a super-repressor form of the IkB-α inhibitory molecule is highly specific to block NF-kB, its use is restrained to cell lines.

It was shown that pharmacological blockade of the IKK2 kinase with an anilinopyrimidine derivative covered by the patent application PCT WO/02/46171 prevented TNF-α induced NF-kB activation in Jurkat leukaemic cells (Frelin and al. Oncogene 2003 (22) pages 8187-8194) and therefore that these derivatives can be used as adjuvant in the treatment of cancer, preferably wherein the cancer is of the colon, AML, rectum, prostate, liver, lung, bronchus, pancreas, brain, head, neck, stomach, skin, kidney, cervix, blood, larynx, esophagus, mouth, pharynx, testes, urinary bladder, ovary or uterus.

DISCLOSURE OF INVENTION

The invention is directed to a pharmaceutical composition comprising the anilinopyrimidine derivative of Formula (I) as an active ingredient which is suitable for encapsulation in hard capsules, and method of treating cancers by oral administration thereof. Accordingly, the invention provides a liquid fill composition of the anilinopyrimidine derivative of Formula (I) for a capsule dosage form. In a preferred embodiment the capsule is an hard capsule. The pharmaceutical composition has a good compliance for patients and allows an high bioavailability in vivo.

DETAILED DESCRIPTION

The liquid fill composition comprises the anilinopyrimidine derivative of Formula (I) and a pharmaceutically acceptable excipient selected from the group consisting of a polyethylene glycol, a glyceryl ester of capric acid or a mixture thereof. In a preferred embodiment the pharmaceutically acceptable excipient is chosen so that the final mixture, i.e. the anilinopyrimidine derivative of Formula (I) and the excipient, is in a liquid form. The capsule composition for encapsulating the liquid fill composition may be gelatin. In a preferred embodiment the capsule is an hard capsule, more preferably an hard gelatine capsule size 00.

Preferably the liquid fill composition is thermoplastic and becomes solid after filling.

A preferred pharmaceutically acceptable excipient is a polyethylene glycol having an average molecular weight comprised between 400 and 800, more preferably comprised between 570 and 630, for example Lutrol E600®.

The liquid fill composition may further comprise a second polyethylene glycol, preferably with an average molecular weight comprised between 3000 and 5000, preferably between 3500 and 4500, for example PEG 4000®.

In a preferred embodiment of the invention, the liquid fill composition comprises between 5% and 15% of the anilinopyrimidine derivative of Formula (I), between 65% and 85% of polyethylene glycol with an average molecular weight of between 3500 and 4500 and between 10% and 20% of polyethylene glycol with an average molecular weight of between 570 and 630.

More preferably, the liquid fill composition comprises 11% of the anilinopyrimidine derivative of Formula (I), 79% of polyethylene glycol with an average molecular weight of between 3500 and 4500 and 10% of polyethylene glycol with an average molecular weight of between 570 and 630.

Alternatively, the pharmaceutically acceptable excipient is selected from a glyceryl ester of capric acid more preferably glyceryl monocaprate, for example Capmul MCM®.

Moreover, the orally administrable pharmaceutical composition according to the present invention may comprise the anilinopyrimidine derivative of Formula (I) and an equimolar mixture of a polyethylene glycol and a glyceryl ester of capric acid, preferably, an equimolar mixture of glyceryl monocaprate and a polyethylene glycol with an average molecular weight comprised between 400 and 800, more preferably a polyethylene glycol with an average molecular weight comprised between 570 and 630.

Preferably, the pharmaceutical composition is formulated in the form of liquid-filled capsules for oral administration.

According to a further aspect of the present invention, it is provided the use of the pharmaceutical composition according to the invention for the preparation of a medicament for the treatment of cancer, preferably Acute Myeloid Leukemia.

Further characteristics of the present invention will be made clear from the following description of some examples supplied for purely illustrative purposes, without limitation.

EXAMPLE 1

Solubilization Tests of an Anilinopyrimidine Derivative of Formula (I)

Different batches of milled drug substance were produced. Different samples of an anilinopyrimidine derivative of Formula (I) were micronised in a jet-milling microniser Pilot-Mill-3 using different nozzles pressure and feeding rates. Nitrogen was used as the processing gas. Table 1 summarizes all the process conditions used for each produced batch and the particle size distribution obtained (measured by LLS).

TABLE 1

| ID Formula (I) starting batch | P nozzle (bar) | P injection (bar) | Feeding rate (rpm) | PSD (µm) | ID Formula (I) produced batch |
|---|---|---|---|---|---|
| 61569-02 | 5 | 5.0 | 2 | d (0.1) 0.90; d (0.5) 2.76; d (0.9) 9.90 | FD050007 |
| O5058086 | 4 | 7.5 | 5 | d (0.1) 1.13; d (0.5) 5.06; d (0.9) 15.81 | FD050092 |

Subsequently in order to analyze the solubility of the anilinopyrimidine of Formula (I) and to identify the preferred excipients, ten solutions of batch FD050007 and ten solution of the starting batch 61569-02 were prepared and analized with a visual solubility test.

A data summary for the anilinopyrimidine derivative of Formula (I) apparent solubility in different excipients is given in Table 2.

TABLE 2

| | Batch | |
|---|---|---|
| ID Solubilizer | Starting batch (61569-02) | Formula (I) milled (FD050007) |
| Transcutol HP (Diethyl. glycol monoct. ether) | Suspension | 26.2 mg/ml |
| Labrasol (caprylocapryoyl macrogol glyceride) | Suspension | 26.3 mg/ml |
| Labrafil M1944CS (oleoyl macrogol glyceride) | Suspension | Suspension |
| Cremophor EL (castor oil-ethylene oxide) | Suspension | Suspension |
| Capmul GMO-50 (glyceril monostearate) | 20.2 mg/ml | 19.6 mg/ml |
| Capmul MCM C10 (glyceril monocaprate) | 59.5 mg/ml | 54 mg/ml |
| Lutrol E600 (PEG 600) | 104 mg/ml | 115 mg/ml |
| Capmul MCM-Lutrol E600 1:1 | 115 mg/ml | 115 mg/ml |
| Vitamin E TPGS | Solid | Solid |
| HP-β-CD | — | 5.75 mg/ml |

As shown in Table 2, the anilinopyrimidine of Formula (I) showed a better solubility when milled, in particular, when milled and then dissolved in Capmul MCM C10, Lutrol E600 and in a mixture Capmul MCM-Lutrol E600 1:1.

EXAMPLE 2

Preparation of Liquid-Filled Capsules Comprising a Micronized Anilinopyrimidine Derivative of Formula (I)

Thermoplastic suspensions of micronized anilinopyrimidine derivative of Formula (I) and of selected excipients among those disclosed in Example 1 (namely Capmul MCM C10, Lutrol E600 and a mixture Capmul MCM-Lutrol E600 1:1) were prepared by homogenization. The thermoplastic suspensions were then used to fill hard gelatine capsules size 00.

After the preparation of the capsules, the thermoplastic suspensions become solid.

Different mixtures were prepared whose composition is given in Table 3. (see next page)

TABLE 3

| ID component (%) | MIXTURES FOR CAPSULE FILLING (ID batch) | | | | | |
|---|---|---|---|---|---|---|
| | FD050011 | FD050012 | FD050013 | FD050111 | FD050124 | FD050125 |
| Formula (I) BATCH FD050007 | 10 | 10 | 10 | — | — | — |
| Formula (I) BATCH FD050092 | — | — | — | 11 | 11 | — |
| Lutrol E600 | 90 | — | 45 | 10 | 10 | 10 |
| Capmul MCM | — | 90 | 45 | — | — | — |
| PEG 4000 | — | — | — | 79 | 79 | 90 |

EXAMPLE 3

Comparative Tests of Bio-Availability

The composition FD050124 in liquid-filled hard gelatine capsules, as described in Example 2, has been compared for bioavailability with an anilinopyrimidine derivative of Formula (I) formulated in a top spray granulate form and in a spray-dried CD-complex form, whose preparations are described below.

Preparation of Top Spray Granulate of an Anilinopyrimidine Derivative of Formula (I):

Micronised anilinopyrimidine derivative of Formula (I), batch FD050007, as obtained in Example 1, was used to produce a granulate by fluid bed top spray granulation. In the top spray granulation process, the powder particles are fluidized in a stream of air and in addition a granulation fluid is sprayed from a nozzle onto the bed of powder. Heated and filtered air is blown through the vessel to fluidize the particles and mix the powder. Granulating fluid is pumped from a reservoir through a spray nozzle positioned over the bed of particles. The fluid causes the primary powder particles to adhere when droplets and particles collide. Sufficient liquid is sprayed to produce granules of the required size; then the spray is turned off, but the heated fluidizing air stream remains on in order to dry the wet granules. Final dilution with lactose and lubricant was necessary to produce a powder with a good flowability and to proceed to sachet filling.

The final granulate composition is shown in Table 4. (see next page)

TABLE 4

| | | Top spray granulated sachets | | |
|---|---|---|---|---|
| ID COMPONENT | % | 5 mg/unit | 50 mg/unit | 100 mg/unit |
| Formula (I) | 1 | 5.0 mg | 50.0 mg | 100.0 mg |
| Granulac 200 | 0.88 | 4.4 mg | 44.0 mg | 88.0 mg |
| Avicel PH 102 | 2.2 | 11.0 mg | 110.0 mg | 220.0 mg |
| Kollidon 90F | 0.22 | 1.1 mg | 11.0 mg | 22.0 mg |
| Tablettose 80 | 95.5 | 478.0 mg | 4780.0 mg | 9560.0 mg |
| Mg Stearate | 0.1 | 0.5 mg | 5.0 mg | 10.0 mg |
| TOT | * | 500 mg | 5000 mg | 10000 mg |

Preparation of Spray-Dried CD Complex of an Anilinopyrimidine Derivatives of Formula (I):

Micronised anilinopyrimidine derivative of Formula (I), batch FD050007, as obtained in Example 1, was used to produce a liquid CD-complex further processed by spray drying.

Spray-drying is a method whereby solutions or slurries are rapidly dried to particulate form by atomizing the liquid in a heated chamber. Spray-drying can be performed using aqueous systems or solvent-based systems under controlled conditions. In principle, a solution of the drug is sprayed at high temperature and pressure into a closed vessel in order to evaporate the liquid and obtain a dried product, which is collected by means of a cyclone where it is separated from the processing gas. The advantage of this technique is that it is possible to obtain an amorphous material, more soluble than the active principle itself.

A 75:25 solution EtOH:$H_2O$ containing 20.25 mM of an anilinopyrimidine derivative of Formula (I) and 50 mM of HP-β-CD (Hydroxy-propyl-β-cyclodextrine—molar ratio 1:2.5) was prepared by dissolving the active principle in EtOH and the HP-β-CD in purified water.

Then, the two solutions were mixed together in the desired ratio to obtain the 75:25 solution EtOH:$H_2O$ and placed in a thermostatic dissolution bath at 40° C. under constant stirring at 250 rpm for 48 h. In all cases, no precipitate was observed. The batches were produced by spray-drying the solution in a Buchi Mini Spray dryer B-191. The operating conditions used are as follows:

| | |
|---|---|
| Inlet temperature | 110° C. |
| Outlet temperature | 64° C. |
| Aspiration | 100% |
| Air flow rate | 700 $m^3$/h |
| P atomization | 7 bar |
| Pump speed | 15 ml/min |
| Nozzle | 0.7 mm |

A further blending step was necessary to produce a physical mixture to be used for sachet filling. The composition of the mixture resulting from this further blending step is summarized in Table 5.

TABLE 5

| ID COMPONENT (%) | Blend for sachets (ID batch) |
|---|---|
| Formula (I) | 9.1 |
| Tablettose 80 | 90.2 |
| Mg Stearate | 0.7 |

This mixture was then subjected, as common pharmaceutical production practice, to a e.g. two step dry compaction by slugging and subsequent milling before obtaining the final blend to be used in sachet filling.

The CD-complex was therefore first blended with half the ratio of Tablettose 80 and compressed into 11 mm tablets. The tablets were then milled through a 0.5 mm screen Fitzpatrick mill (FS75) and again compressed and screened. Finally the dry granulate produced in this way was mixed with the other half of Tablettose 80 and Mg stearate as lubricant.

The final blend composition is shown in Table 6. (see next page)

TABLE 6

| | | Spray dried CD-complex sachets | | |
|---|---|---|---|---|
| ID COMPONENT | % | 5 mg/unit | 50 mg/unit | 100 mg/unit |
| Formula (I) | 1 | 5.0 mg | 50.0 mg | 100.0 mg |
| HP-β-CD | 8.1 | 40.5 mg | 405.0 mg | 810.0 mg |
| Tablettose 80 | 90.2 | 451.0 mg | 4510.0 mg | 9020.0 mg |
| Mg Stearate | 0.7 | 3.5 mg | 35.0 mg | 70.0 mg |
| TOT | * | 500 mg | 5000 mg | 10000 mg |

Bioavailability Comparison:

Liquid-filled capsules, granulate and Spray dried CD-complex stored under ICH conditions have been shown to be stable after 6 months up to 40° C.±75% RH.

Three formulations were orally tested in rats, as

Formulation (a): Spray dried CD complex of an anilinopyrimidine derivative of Formula (I);

Formulation (b): an anilinopyrimidine derivative of Formula (I) in granules;

Formulation (c): an anilinopyrimidine derivative of Formula (I) in liquid-filled capsules.

The liquid-filled capsules gave the highest exposure in vivo; the relative bioavailability of the drug was found to be about twice higher than that obtained with the other two formulations, top spray granules and cyclodextrin complex, and about 20% higher than that obtained with micronised anilinopyrimidine derivative of Formula (I) suspension as shown in Table 7.

TABLE 7

| | Formulation (a) 10 mg/kg | Formulation (b) 10 mg/kg | Formulation (c) 1 cps/rat 11.3 mg/kg |
|---|---|---|---|
| Cmax (ng/mL) | 4253 | 3945 | 7475 |
| tmax (h) | 2 | 4 | 4 |
| AUC (h * ng/mL) | 36865 | 35923 | 77580 |
| t½ (h) | 4.2 | 3.6 | 4.2 |
| MRT (h) | 6.8 | 8.2 | 9.9 |
| F rel | 0.66 | 0.64 | 1.22 |

The invention claimed is:

1. An oral pharmaceutical composition comprising a capsule dosage form containing a liquid fill composition said liquid composition comprising between 5% and 15% of an anilinopyrimidine of Formula (I) as active ingredient

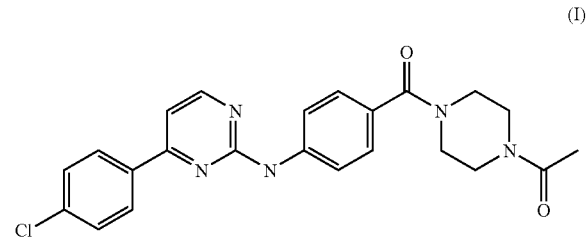

between 65% and 85% of a polyethylene glycol with an average molecular weight of between 3500 and 4500, and between 10% and 20% of a polyethylene glycol with an average molecular weight of between 570 to 630.

2. The pharmaceutical composition according to claim 1, wherein said pharmaceutically acceptable excipient is in a liquid form.

3. The pharmaceutical composition according to claim 1, wherein it comprises 11% of the anilinopyrimidine of Formula (I), 79% of the polyethylene glycol with an average molecular weight of between 3500 and 4500, and 10% of the polyethylene glycol with an average molecular weight of between 570 to 630.

4. The pharmaceutical composition according to claim 1, further comprising a glyceryl ester of capric acid.

5. The pharmaceutical composition according to claim 4, wherein it comprises an equimolar mixture of the glyceryl ester of capric acid and a polyethylene glycol with an average molecular weight comprised between 570 and 630.

6. The pharmaceutical composition according to claim 1, wherein the capsule dosage form is a liquid-filled capsule.

7. The pharmaceutical composition according to claim 1, wherein the liquid fill composition is a thermoplastic suspension.

8. The pharmaceutical composition according to claim 7, wherein the thermoplastic suspension becomes solid after filling.

9. The pharmaceutical composition according claim 6, wherein said capsule dosage form is a hard capsule.

10. The pharmaceutical composition according to claim 9, wherein said capsule dosage form is a hard gelatine capsule size 00.

11. A method of treating a cancer responsive to inhibition of IKK comprising administering a therapeutically effective amount of an oral pharmaceutical composition of claim 1 to an individual in need thereof.

12. The method according to claim 11, wherein the cancer is acute myeloid leukemia.

13. The pharmaceutical composition of claim 5 wherein the glyceryl ester of capric acid is glyceryl monocaprate.

* * * * *